United States Patent [19]
McNeil et al.

[11] Patent Number: 5,703,692
[45] Date of Patent: Dec. 30, 1997

[54] LENS SCATTEROMETER SYSTEM EMPLOYING SOURCE LIGHT BEAM SCANNING MEANS

[75] Inventors: John R. McNeil; S. Sohail H. Naqvi; Scott R. Wilson, all of Albuquerque, N. Mex.

[73] Assignee: Bio-Rad Laboratories, Inc., Hercules, Calif.

[21] Appl. No.: 510,990

[22] Filed: Aug. 3, 1995

[51] Int. Cl.$^6$ ............................. G01N 21/47; G01B 11/02
[52] U.S. Cl. ................................. 356/445; 356/446
[58] Field of Search ............................. 356/445, 446, 356/371

[56] References Cited

U.S. PATENT DOCUMENTS

| | | | |
|---|---|---|---|
| 4,199,219 | 4/1980 | Suzki et al. | 356/445 X |
| 4,583,858 | 4/1986 | Lebling et al. | 356/446 X |
| 4,710,642 | 12/1987 | McNeil | 250/571 |
| 4,806,018 | 2/1989 | Falk | 356/446 |
| 5,241,369 | 8/1993 | McNeil et al. | 356/445 |

FOREIGN PATENT DOCUMENTS

| | | | |
|---|---|---|---|
| 26571566 | 6/1978 | Germany | 356/445 |
| 1326881 | 7/1987 | U.S.S.R. | 356/371 |

OTHER PUBLICATIONS

Murnane, Michael R. et al., "Developed PHotoresist Metrology Using Scatterometry," Proceeding of the SPIE, Integrated Circuit Metrology, Inspection, and Process Control VIII, vol. 2196, pp. 47–59 (1994).

Murnane, Michael R. et al., "Scattrometry for 0.24um–0.70um Developed Photoresist Metrology," Proceedings of the SPIE, Integrated Circuit Metrology, Inspection, and Process Control IX, vol. 2439, pp. 427–436 (1995).

Primary Examiner—Vincent P. McGraw
Attorney, Agent, or Firm—William E. Hein

[57] ABSTRACT

An optical scatterometer system enables illumination of a sample material at various angles of incidence without rotating or otherwise moving the sample material.

30 Claims, 16 Drawing Sheets

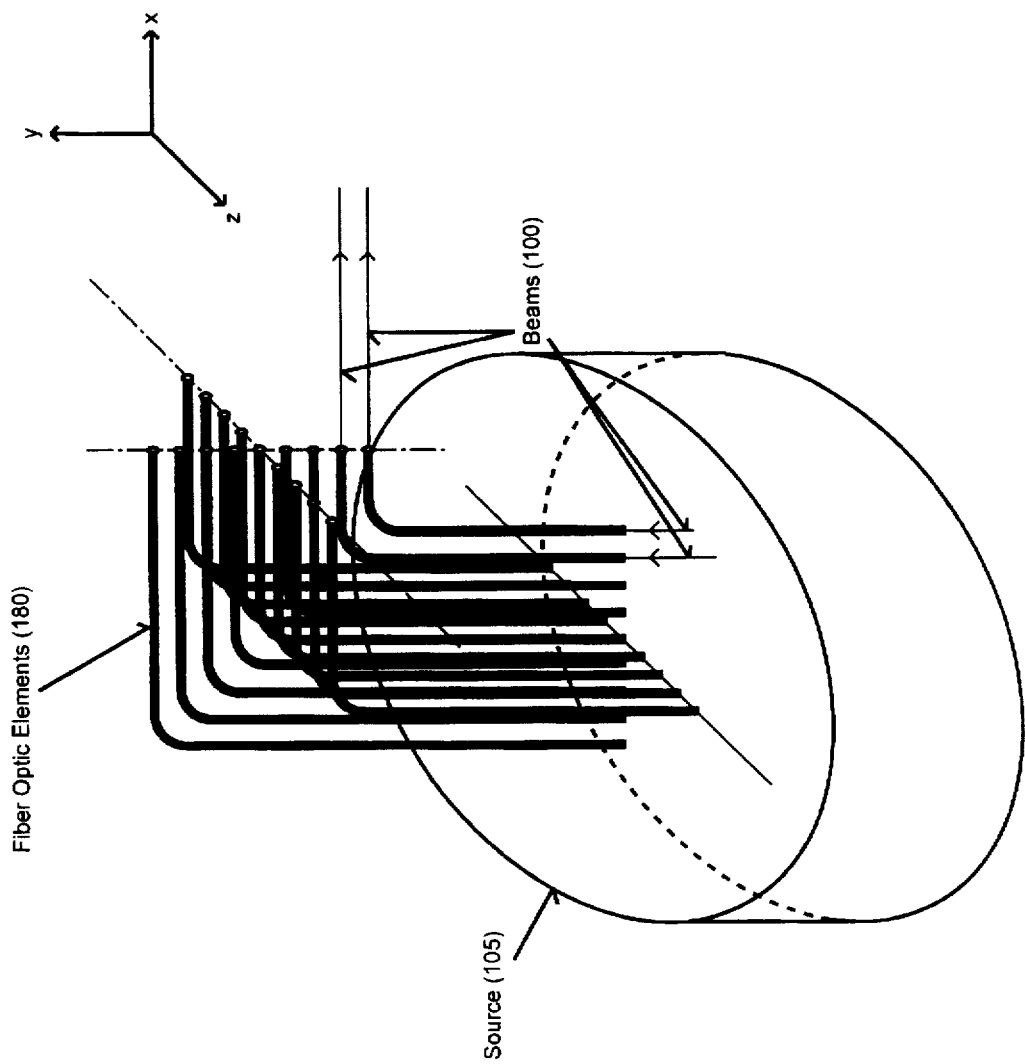

LENS SCATTEROMETER SYSTEM EMPLOYING SOURCE LIGHT BEAM SCANNING MEANS

REFERENCE TO RELATED PATENTS

This application is related to and incorporates by reference the subject matter of U.S. Pat. Nos. 4,710,642, 5,164,790, and 5,241,369.

BACKGROUND AND SUMMARY OF THE INVENTION

This invention relates generally to scatterometers and more particularly to a lens scatterometer system that provides for illumination of a sample at different angles of incidence without the necessity of rotating, tilting or otherwise moving the sample during the course of a scatterometer measurement.

Scatterometer arrangements, like those described in the prior art patents cited above, have been used for characterizing the microstructure of microelectonic and optoelectronic semiconductor materials, computer hard disks, optical disks, finely polished optical components, and other materials having lateral dimensions in the range of tens of microns to less than one micron.

Exemplary of the prior art are two publications. The first is by Michael R. Murnane, et. al., "Developed Photoresist Metrology Using Scatterometry", Proceedings of the SPIE, Integrated Circuit Metrology, Inspection, and Process Control VIII, Vol 2196, pp 47–59 (1994); the second is by Michael R. Murnane, et. al., "Scatterometry for 0.24 µm–0.70 µm Developed Photoresist Metrology", Proceedings of the SPIE, Integrated Circuit Metrology, Inspection, and Process Control IX, Vol 2439, pp 427–436 (1995). This referenced prior art extends the capability of the scatterometer measurements to enable characterization of structure having lateral dimensions that are sub-tenth-micron. The prior art scatterometer arrangement discussed in the literature is disadvantageous in that it requires rotation of the sample while performing a scatterometer measurement. This requirement precludes their use in applications in which the sample must remain stationary. In addition, the two rotation stages employed in this prior art scatterometer represents a mechanical complexity, which can result in undesirable optical and mechanical misalignment. Finally, the sample rotation required in this prior art scatterometer necessitates increased sample handling, thus increasing the risk of damage to the sample.

It is therefore the principle object of the present invention to provide a scatterometer system that enables illumination of a sample at various angles of incidence without rotating or otherwise moving the sample.

BRIEF DESCRIPTION OF THE DRAWINGS

FIG. 6b is a pictorial diagram of a portion of a lens scatterometer system in accordance with the present invention, illustrating the use of a two dimensional fiber optic assembly for characterizing light that is conically diffracted from the sample.

DETAILED DESCRIPTION OF THE PREFERRED EMBODIMENTS

Figure 1:
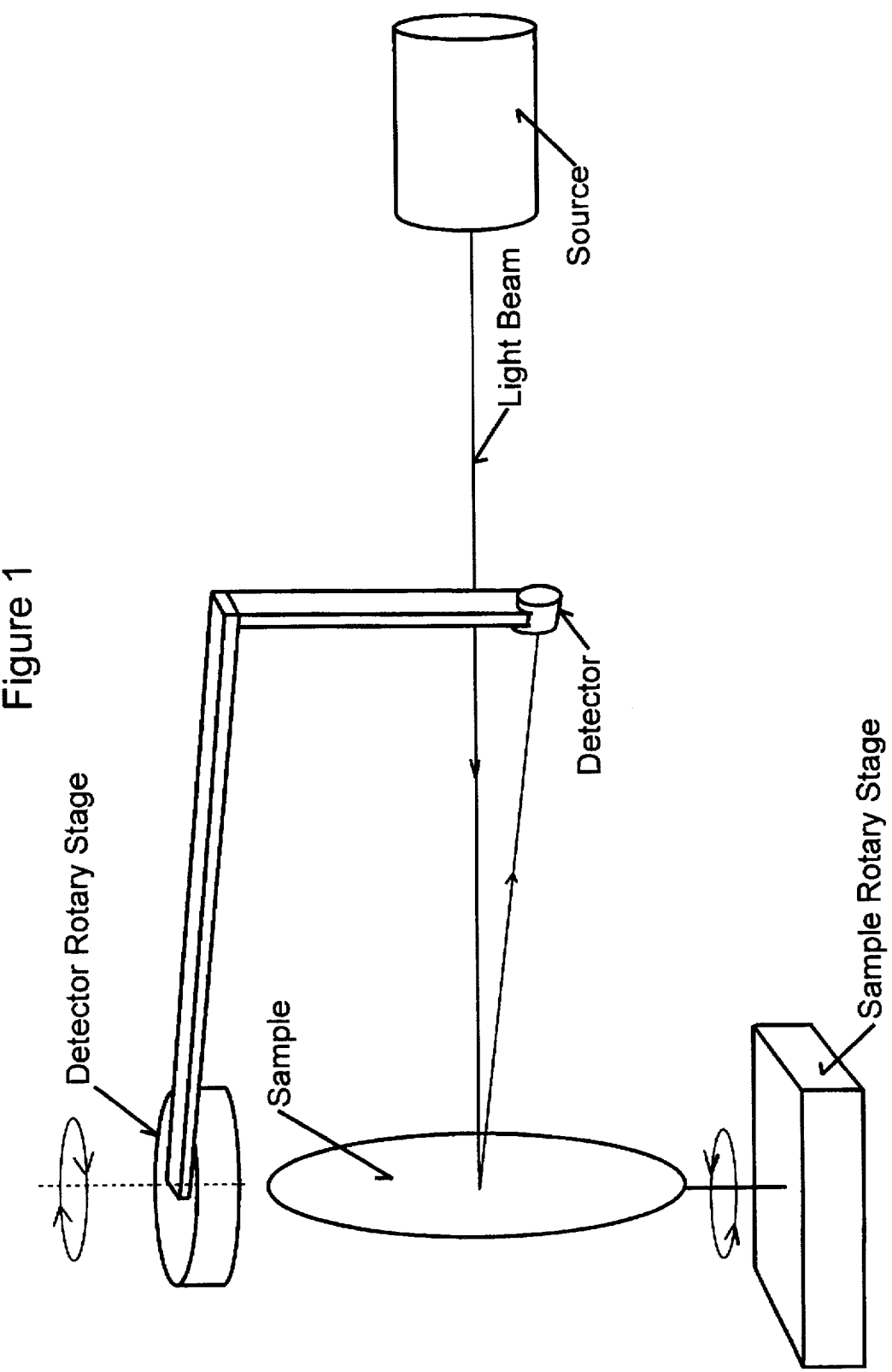
FIG. 1 is a pictorial diagram illustrating a prior art scatterometer system employing a single detector and two rotation stages to move both the sample and the detector.

The present invention may be understood by first referring to the prior art scatterometer system illustrated in FIG. 1, hereafter referred to as the 2-Θ scatterometer arrangement. In this scatterometer arrangement two rotational stages are incorporated. One stage, called the "sample stage" is utilized to rotate the sample, and one stage, called the "detector stage" is utilized to rotate a detector. Typically in this 2-Θ scatterometer arrangement the rotation axes of the two stages are coincident, although this is not required. The sample is illuminated with a light beam that is incident on the sample at a point that is also on the rotation axis of the sample; in other words the front surface of the sample contains the axis of rotation of this sample stage. In this manner the angle of incidence of the light illuminating the sample can be made to vary over a range in a desired manner, and this can be controlled, for example, by a computer that is connected to the sample stage. Further, as the angle of incidence is changed by activating the sample stage, the detector stage is activated to move the detector in a desired manner. The two stages are activated either simultaneously, or practically simultaneously.

As explained previously, the 2-Θ scatterometer arrangement is especially useful for characterizing the light scattered and diffracted from samples which are comprised of structure that is periodic. When monochromatic, plane wave light is incident upon the periodic structure, the light is diffracted into orders at angles governed by the simple grating equation, $$\sin \Theta + \sin \Theta' = n\lambda/d$$

In this expression, Θ is the angle of incidence of the light, Θ' is the angle made by the diffraction order, n is the order number, λ, is the wavelength of the light, and d is the period or pitch of the structure that is illuminated. This relationship is well known and discussed in text books on optics.

The 2-Θ scatterometer thus monitors the intensity of a single diffraction order as a function of the angle of incidence of the illuminating light beam. The intensity variation of the 0-order as well as higher diffraction orders from the sample can be monitored in this manner, and this provides information which is useful for determining the properties of the sample which is illuminated. Because the properties of a sample are determined by the process used to fabricate the sample, the information is also useful as an indirect monitor of the process. This methodology is described in the literature of semiconductor processing.

Note that the light beam used to illuminate the sample might be the output from a laser or it might be some other appropriate beam of radiation that can be directed to illuminate the sample. Typically continuous, low power lasers such as He-Ne, Ar-ion, He-Cd and semiconductor diodes are used for the source of the light beam, although other sources of radiation might be used equally well in the scatterometer arrangement described here. The wavelength of the sources might range from x-ray through the visible and microwave regions, to the long wavelength region which corresponds to frequencies of just a few Hz. Generally, larger wavelengths provide for characterizing samples that have structure of larger dimensions. The following discussion will use the terminology "beam" or "light beam" to refer to the radiation that illuminates the sample that is within this wavelength region. Similarly, it is understood that the different diffraction orders that result from illuminating the sample with the beam will also be called "diffracted beams".

A shortcoming of the prior art 2-Θ scatterometer arrangement illustrated in FIG. 1 is that the sample must be rotated in the process of performing a scatterometer measurement. The angular range over which the sample is rotated in this prior art configuration is typically 40 degrees or more, and in some applications of the 2-Θ scatterometer arrangement the sample must be rotated ±40 degrees or more (i.e. a total of 80 degrees or more). Because the axis of rotation of the sample is parallel to, and included in the surface of the sample, this rotation precludes application of the prior art 2-Θ scatterometer arrangement in situations in which the sample must necessarily be stationary. This occurs practically at all steps in processing many materials, including semiconductor materials, storage media, and the like. For example, in processing semiconductor wafers in a vacuum environment, in which the wafer can not be moved existing processing equipment and associated processing techniques would require extensive modification to accommodate wafer rotation. Such modifications would be impractical.

Additionally, the two rotation stages utilized in the prior art 2-Θ scatterometer arrangement represent mechanical complexity. Eliminating one or both of them would represent a significant simplification in maintaining optical and mechanical alignment.

Another shortcoming of the sample rotation in implementing the prior art 2-Θ scatterometer arrangement illustrated in FIG. 1 is that the two stages involve mechanical motion, and this generates particulate contamination. Because the sample is located near to the stages, contamination levels on the sample can increase because of this.

Finally, sample rotation in the prior art configuration of FIG. 1 requires increased levels of sample handling, which in turn increases the risk of damaging the sample. The sample must be fixed in a holder that will sufficiently secure the sample for rotation, and this involves more handling of the sample compared to an arrangement in which the sample is stationary. Similarly, increased handling requires more time before the sample can be examined.

Figure 2:
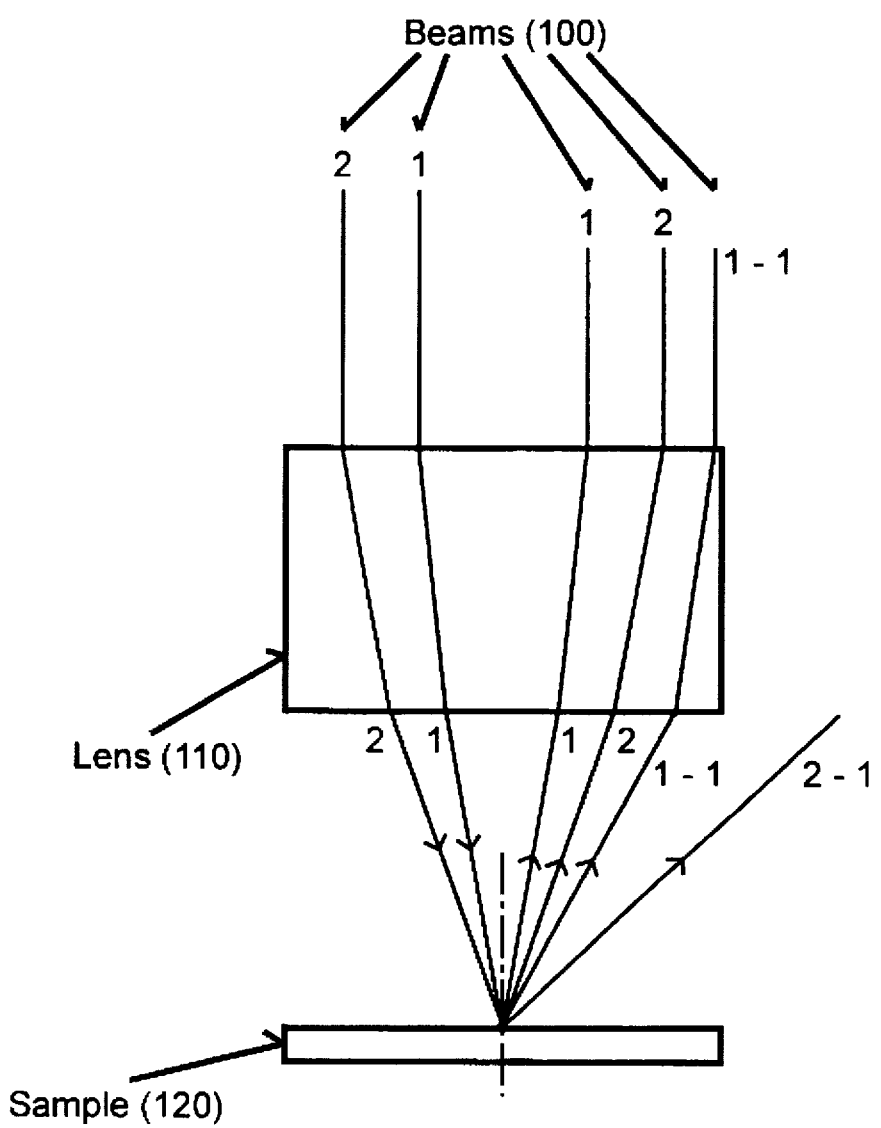
FIG. 2 is a pictorial diagram of a lens in accordance with the present invention, illustrating use of the lens to provide illumination of a sample at different angles of incidence and to collect the light that is diffracted from the sample, in accordance with the present invention.

FIG. 2 illustrates how a beam (100) can be directed to different points of the entrance aperture of a lens (110) and be transmitted through the lens (110) to illuminate a sample (120) at different angles of incidence. The angle of incidence depends upon the radial location of the beam in the entrance aperture of the lens. Only two beams (100) are shown in the FIG. 2 for purposes of illustration; these two beams (100) are labeled "1" and "2" in FIG. 2. The invention would typically utilize many beams to illuminate the sample (120). For simplicity of illustration, the beams (100) are shown to travel in directions that are parallel to the axis of the lens (110) prior to entering the lens (110). However, the beams are not required to travel parallel to the axis of the lens (110) prior to entering the lens (110), nor are the beams required to be parallel to each other prior to entering the lens. The portion of the sample (120) which is to be characterized is located in the image plane of the lens at the point where the beams are imaged to a common point. In the special case in which the beams travel parallel to each other prior to entering the lens, the sample (120) is placed in the back focal plane of the lens; the back focal plane is the same as the image plane in this situation. More specifically, in the case in which the beams are all parallel to the lens axis, the sample (120) is located at the back focal point of the lens.

It is understood that in application of the invention discussed herein, many beams are directed to the entrance aperture of the lens (110) to subsequently provide illumination of the sample (120) at many different angles of incidence. In one embodiment of the present invention, the beams are individually activated in sequence, such that only one beam illuminates the sample (120) at one specific time and at one specific angle of incidence. Alternatively, more than one of the beams can be activated simultaneously, with each beam illuminating the sample (120) at a corresponding angle of incidence. A third embodiment of the present invention utilizes a single beam that is translated across the entrance aperture of the lens (110). This achieves the effect of illuminating the sample (120) with many beams at many different angles of incidence over a period of time. A fourth embodiment of the present invention utilizes a linear beam to illuminate the entrance aperture of the lens (110). This achieves the effect of illuminating the sample (120) with a large number of beams at a continuum of angles of incidence. The light detection configuration, in part, determines the sample illumination arrangement that is utilized.

Typically the diameter of the beam (100) is much smaller than the aperture of the lens (110). For example, in one implementation the output of a He-Ne laser is approximately 1 mm in diameter, and the lens entrance aperture is in the range of 25 mm to 100 mm. Both the beam diameter and the lens entrance aperture can be scaled larger or smaller by use of appropriate optical elements. In this manner, the beam that exits the lens illuminates the sample at substantially a single angle of incidence.

The lens (110) that is utilized in the present invention substantially determines the range over which the angle of incidence of the beam can be varied. Specifically, the f-number (f/#) of the lens will determine the maximum angle of incidence the beam can have in illuminating the sample. For example, in the case of beams that enter the lens parallel to the lens axis, the maximum angle of incidence, $\Theta$, is given by $\sin^{-1}\{1/(2f/\#)\}$. Lenses are commercially available that have an f/# of 0.74 and an aperture of 50 mm diameter. A beam that enters this lens traveling parallel to the lens axis and 25 mm from the lens center illuminates the sample with an angle of incidence of approximately 42.5 degrees. Beams that pass through the lens at smaller radial positions, closer to the center of the lens, exit the lens to illuminate the sample at smaller angles of incidence. The relation between the location of the beam in the lens entrance aperture and the angle of incidence of the beam at the sample is determined by the lens design. Similar relations exist in the case of the lens being cylindrical as opposed to spherical.

The light that illuminates the sample is diffracted by the sample into two or more beams. There are two sets of diffracted beams: beams that are transmitted into the sample and beams that are reflected from the sample. The two so-called 0-order diffracted beams or orders, corresponding to n=0 in the simple grating equation, will always exist, with one transmitted into the sample and the other reflected from the sample. Higher order diffraction from the sample, e.g. the n=±1, ±2, etc. orders that are reflected and transmitted may or may not be present; the existence of these higher orders is governed by the simple grating equation. The intensity of the diffracted beams is extremely sensitive to the structure comprising the sample. Specifically, the pitch of the lines comprising the diffracting structure, as well as their width, height, and sidewall curvature in the case of the sample being a relief grating, are contributing factors that determine the diffraction characteristics of the sample. If the sample is comprised of a phase grating, such as exposed, but undeveloped photoresist, the pitch and width of the latent image structure determine the diffraction characteristics. Details of the diffraction characteristics are described in the literature.

One or more of the diffracted beams which are reflected from the sample enter the bottom of the lens. The reflected 0-order beams will enter the lens, as shown in FIG. 2; this is illustrated by beams 1-0 and 2-0 in the figure for the two beams 1 and 2, respectively. The higher diffraction orders reflected beams will enter the lens provided their diffraction angle is within the acceptance angle of the lens. This is illustrated in FIG. 2 by diffraction order 1-1 shown entering the lens, and diffraction order 2-1 shown not entering the lens (110). Diffraction order 1-1 corresponds to one of the 1st-order diffracted beams from the incident beam 1, and diffraction order 2-1 corresponds to one of the 1st-order diffracted beams from the incident beam 2. The beams which enter the lens transmit through the lens and exit the lens as illustrated in FIG. 2. For simplicity, not all of the reflected diffraction orders, and none of the transmitted diffraction orders are illustrated in FIG. 2.

It is understood that the construction details of the lens (110) of the invention vary significantly, depending, for example, upon the performance requirements of the lens (110). For example, the wavelength of the beam (100) will determine the material properties of the elements which comprise the lens (110). The lens (110) will typically be comprised of transparent glass for wavelengths of the beam (100) which are within the visible region. For wavelengths which are significantly shorter than those of the visible region, some or all of the elements which comprise the lens (110) will necessarily be reflecting to the beam (100). It is further understood that other performance requirements of the lens (110) will determine details of the construction and characteristics of the lens (110).

Figure 3A:
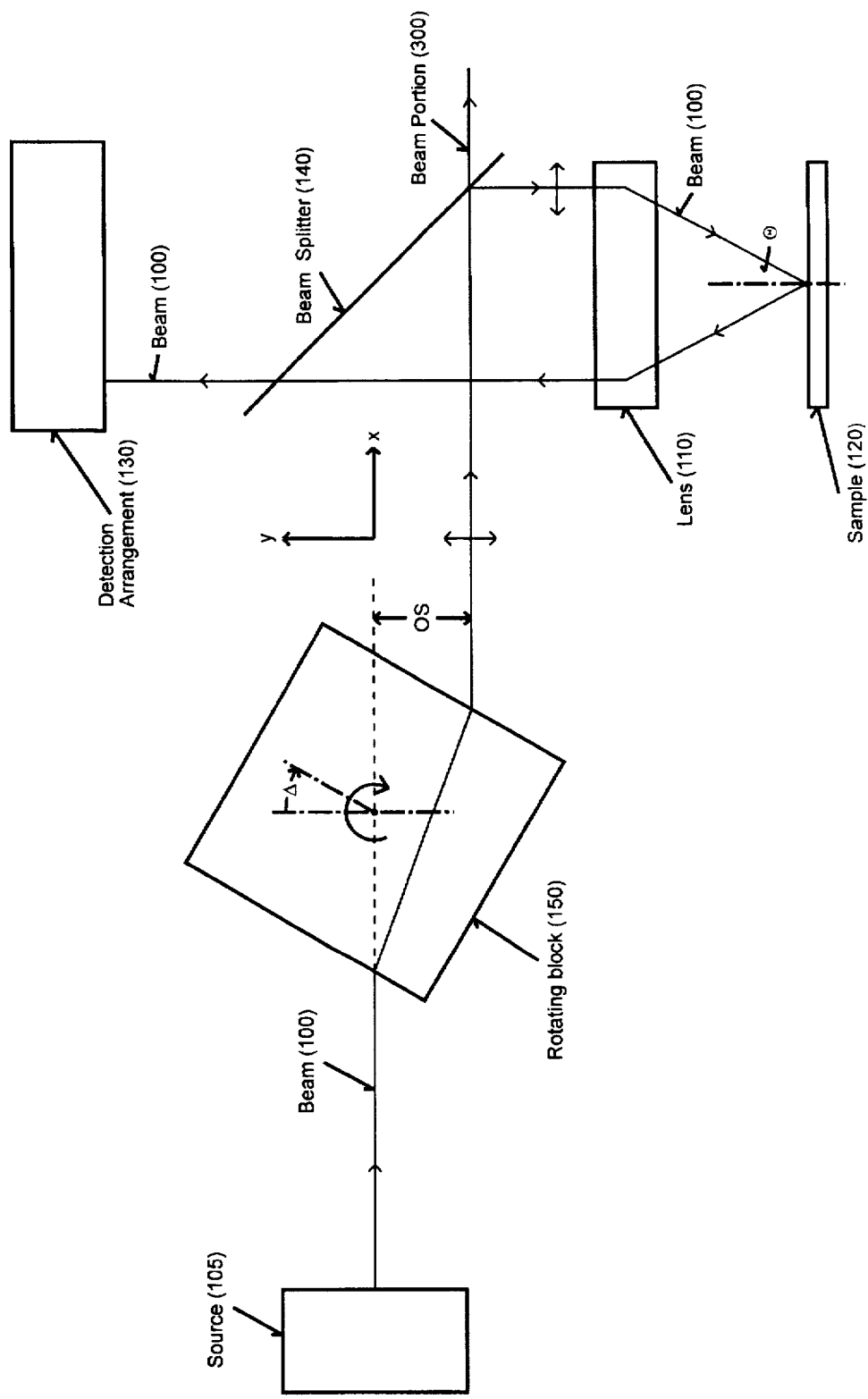
FIG. 3a is a pictorial diagram of a lens scatterometer system in accordance with the present invention, illustrating the use of a lens, beam splitter, rotating block, and light detection system for characterizing the light that is diffracted from the sample.
Figure 3B:
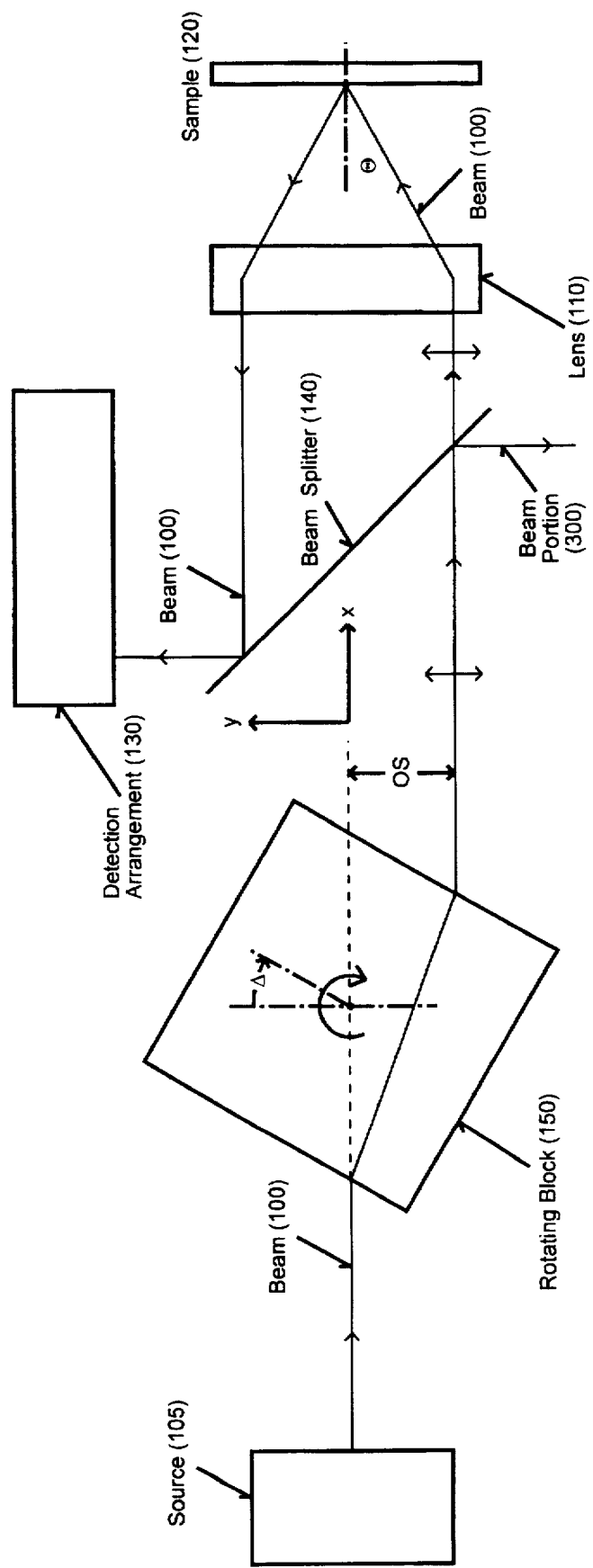
FIG. 3b is a pictorial diagram of a lens scatterometer system in accordance with the present invention, illustrating the use of a lens, beam splitter, rotating block, and light detection system for characterizing the light that is diffracted from the sample.

FIGS. 3a and 3b illustrate scatterometer arrangements that utilize a rotating block (150) to provide a means of translating the beam from the source (105) to different points of the entrance aperture of the lens (110), and thus to illuminate the sample (120) at different angles of incidence, $\Theta$. These arrangements comprise lens scatterometer systems and represent an improvement over the 2-$\Theta$ scatterometer. The lens scatterometer arrangements provide a means of changing the angle of incidence, $\Theta$, of the beam at the sample (120) without moving the sample (120).

The lens system scatterometer arrangements illustrated in FIGS. 3a and 3b are comprised of the lens system and sample arrangement previously described, together with a detection arrangement (130), a beam splitter arrangement (140), and a rotating block (150) that rotates about a single axis. The x-y axes of a coordinate system are illustrated in the figures. The beam (100) is in the x-y plane as it originates from the source. The rotating block is transparent at the wavelength of the beam. In the arrangement the beam from the source (105) propagates through the rotating block to different points on the beam splitter. At the beam splitter the beam is partially reflected. A portion of the beam is directed to different points of the entrance aperture of the lens (110) to illuminate the sample (120) at different angles of incidence, $\Theta$.

In FIG. 3a the portion of the beam (100) that is reflected from the beam splitter is directed toward the lens; the portion of the beam (100) that is transmitted by the beam splitter is called the beam portion (300). In general, the block (150) rotates about an axis that is not necessarily parallel to the beam propagation direction. The specific arrangement of the invention illustrated in FIG. 3a has the block rotation axis being perpendicular to the x-y plane. In addition, the beam splitter (140) is perpendicular to the x-y plane. The faces of the block (150) at which the beam enters and exits are parallel, and they are also both parallel to the axis of rotation. Additionally, these faces of the block as well as the surfaces of the beam splitter (140) are perpendicular to the x-y plane. Thus the beam (100) remains in the x-y plane after transmission through the block (150) and after reflection from the beam splitter. The beam is offset after transmission through the block, shown as OS in FIG. 3a, and the amount of offset is dependent upon the rotation angle, Δ, of the block about its axis of rotation. This relation is easily calculated and is described in optics text books. In the specific arrangement illustrated in FIG. 3a, the block rotation causes the beam to be offset from, and parallel to, the beam prior to transmitting through the block, thus remaining in the x-y plane. In addition, the axis of the lens (110) is in the x-y plane in the arrangement illustrated in FIG. 3a. Thus the beam is translated to different points along a line in the entrance aperture of the lens, and the beam locations at different angles of incidence, Θ, at the sample (120) location also lie in the x-y plane. In the arrangement illustrated in FIG. 3a, the beam portion (300) is directed to a beam dump or other device and is not utilized.

It is understood that more generally the rotation axis of the block (150), the axis of the lens (110), and the surfaces of the beam splitter (140) are not required to be perpendicular or parallel to the x-y plane as described above, in which case the beam locations at different angles of incidence Θ define a surface that is not necessarily located in the x-y plane. It is also understood that the block (150) can have a shape that is not exactly as illustrated in FIG. 3a. For example, the block (150) can be rectangular in two of its dimensions, as opposed to the square shape illustrated in FIG. 3a. More generally, the block (150) can be comprised of a shape that has a total number of faces different than four, as illustrated in FIG. 3a.

The reflected diffraction orders pass through the lens (110) as previously described to the beam splitter (140); for simplicity, only the reflected 0-order is illustrated in FIG. 3a. At the beam splitter the reflected diffraction orders are partially transmitted by the beam splitter (140) to the detection system (130) where their intensities are measured. Measurements of the diffraction order intensifies are made for each of a number of values of Δ and corresponding beam (100) angles of incidence Θ. The primary purpose of the invention illustrated in FIG. 3a, namely to provide a means of illuminating the sample at different angles of incidence and measuring the intensities of the reflected diffraction orders, without requiring the sample to be moved is thereby accomplished.

FIG. 3b illustrates essentially the same invention as illustrated in FIG. 3a. In the arrangement of FIG. 3b, the portion of the beam (100) from the source that is transmitted by the beam splitter (140) is directed toward the lens (110) to illuminate the sample (120); the portion of the beam (100) that is reflected by the beam splitter is called the beam portion (300). The reflected diffraction orders which pass through the lens to the beam splitter are partially reflected to the detection system (130). In the arrangement illustrated in FIG. 3b, the beam portion (300) is directed to a beam dump or other device and is not utilized. Otherwise the invention is essentially the same as that illustrated in FIG. 3a, with the primary purpose of providing a means of illuminating the sample at different angles of incidence Θ and measuring the intensities of the reflected diffraction orders without moving the sample.

Figure 3C:
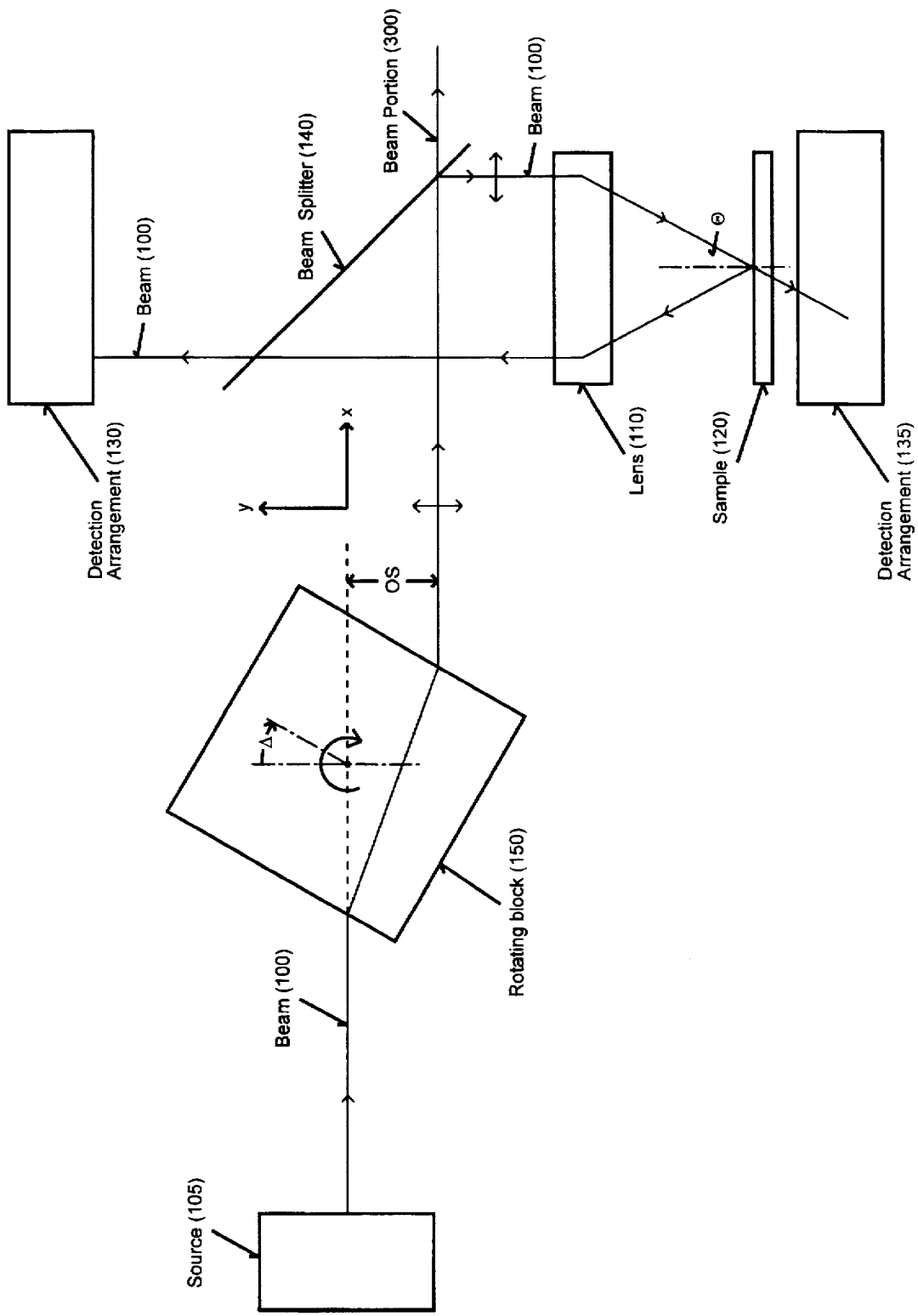
FIG. 3c is a pictorial diagram of a lens scatterometer system in accordance with the present invention, illustrating the use of a lens, beam splitter, rotating block, and two light detection systems for characterizing the light that is diffracted from the sample.

FIG. 3c illustrates how an additional detection system (135) can be utilized with the invention of either FIG. 3a or 3b. The additional detection system is shown used in the arrangement of FIG. 3a for illustrative purposes. The additional detection system (135) is used on the side of the sample (120) opposite to the side which is illuminated; i.e., below the sample (120). In this manner the arrangement can characterize the intensities of diffraction orders that are transmitted by the sample (120). This measurement can be performed over a range of incident angles of the beam without requiring the sample (120) to be moved. Note that the additional detection system (135) below the sample (120) can be utilized independently of the detection system (130) located above the sample (120) that measures the intensities of the reflected diffraction orders; the scatterometer arrangement can be configured to have either or both of the detection systems. The detection system (135) below the sample (120) is not required to be identical to the detection system (130) above the sample (120). For example, the detection system (135) below the sample (120) might include lower quality optical elements, such as lenses of lessor optical quality than the lens (110).

The light detection systems (130) and (135) of FIGS. 3a, 3b, and 3c contain a detector device. The detector device can be comprised of a simple, single element such as a Si photodiode, a photomultiplier, or other element appropriate for detecting the wavelength and intensifies of the reflected or transmitted diffracted beams. A single element detector provides an integrated measurement of all the diffraction order intensities. Alternatively, the detector device can be comprised of a one-dimensional or two-dimensional detector array, such as a ccd array, a photodiode array, or other one-dimensional or two-dimensional detector array appropriate for the wavelength and intensities of the diffracted beams. Use of a detector array provides spatially resolved intensity measurements of the individual diffraction orders and thus provides additional information compared to that obtained in integrated measurement. Similarly, the detector device can be a videcon, nuvecon, or other similar detection element that provides spatially resolved intensity measurements of the diffraction orders. The detection systems (130) and (135) might also contain additional elements, such as lenses. In some situations the detection systems (130) and (135) might be considered to be a camera that utilizes either of the detector devices previously mentioned.

Figure 4:
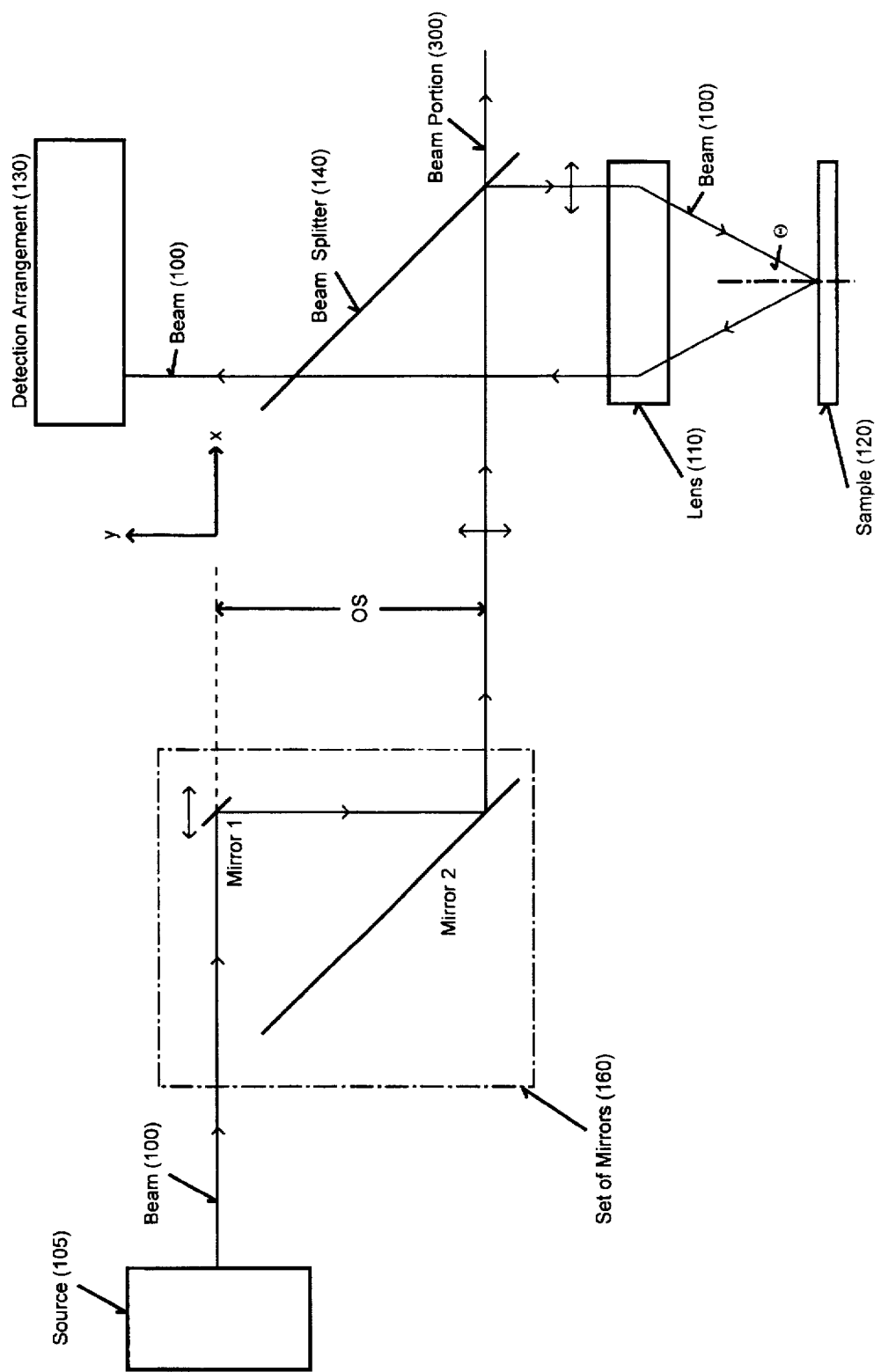
FIG. 4 is a pictorial diagram of a lens scatterometer system in accordance with the present invention, illustrating the use of a lens, beam splitter, mirror assembly, and light detection system for characterizing the light that is diffracted from the sample.

FIG. 4 illustrates how the lens system scatterometer invention described in FIG. 3a can utilize a set of mirrors (160) in place of the rotating block (150) to direct the beam to different points of the entrance aperture of the lens (110), and thus to illuminate the sample (120) at different angles of incidence. In FIG. 4 the set of mirrors (160) is comprised of two or more mirrors. In the arrangement, one or more mirrors of the set of mirrors (160) translates in a manner to cause the beam at the beam splitter (140) to be offset from the same beam prior to encountering the set of mirrors. The amount of beam offset is dependent upon the amount of mirror translation. This, in turn, causes the beam to pass through the lens entrance aperture at different locations, and thus to illuminate the sample (120) at different angles of incidence, similar to the description of the invention of FIG. 3a, b, and c. FIG. 4 illustrates just one manner of achieving this beam offset. In the arrangement illustrated in FIG. 4, this is achieved by translating mirror 1 and keeping mirror 2 fixed in position. In this configuration, the beam (100) is reflected from mirror 1 to different points on mirror 2, reflected from mirror 2 to different points on the beam splitter (140), and it subsequently passes through the lens (110) at different aperture locations, to thereby illuminate the sample (120) at different angles of incidence. The angle of incidence, Θ, depends upon the position of mirror 1. The same effect can be achieved by translating mirror 2 and keeping mirror 1 fixed in position. In this manner the set of mirrors provides a similar function as the rotating block (150) in the invention illustrated in FIGS. 3a, b, and c. Otherwise the inventions of FIGS. 3a and 4 are essentially the same. A set of mirrors can be similarly utilized in place of the rotating block of the inventions described in FIGS. 3b and 3c. It is understood that more generally some or all the mirrors of the set of mirrors (160) can be non-planar, and that some or all can be made to rotate. Other manners of translating or rotating mirrors which comprise a set of mirrors (160) can be envisioned to provide a means of translating the beam to different points in the entrance aperture of the lens (110), and thus to provide sample illumination at different angles of incidence Θ without requiring the sample (120) to be moved.

Other means can be envisioned of directing the beam to different points of the entrance aperture of the lens (110). The two methods previously discussed, which involve the rotating block (150) and the set of mirrors (160) are but two means of achieving this.

Figure 5A:
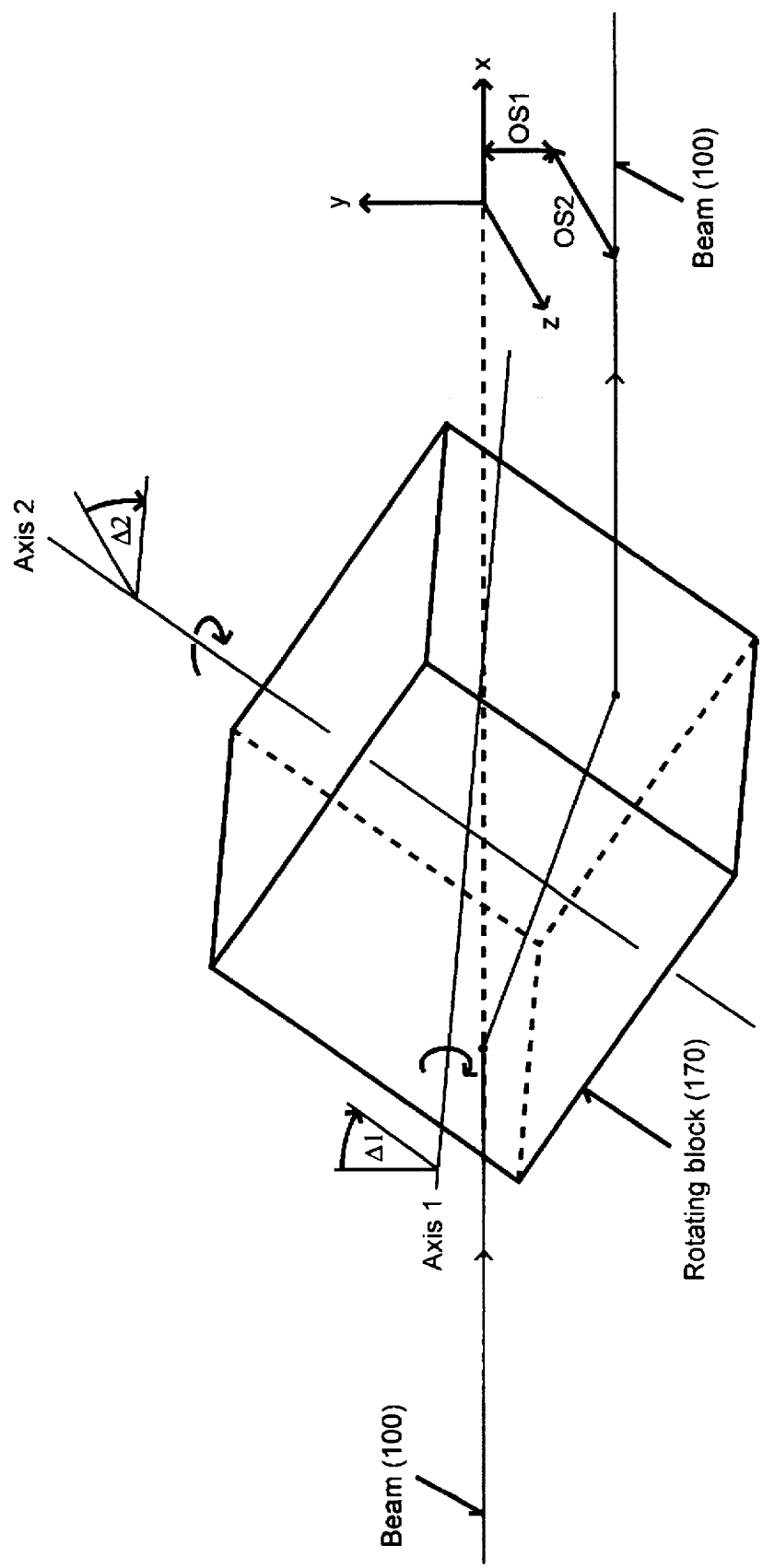
FIG. 5a is a pictorial diagram of a portion of a lens scatterometer system in accordance with the present invention, illustrating a block that is rotated about two axes that is used for characterizing light that is conically diffracted from the sample.

FIG. 5a illustrates a modified version of the rotating block (150) of the inventions illustrated in FIGS. 3a, 3b, and 3c. The rotating block (170) is mounted in a manner that provides rotation about two axes, shown as axis 1 and axis 2 in FIG. 5a. A typical application would include the two axes being orthogonal. For example, mounting the rotating block (170) in a gimbals arrangement would provide such orthogonal axes of rotation. Under this biaxial rotation, the beam (100) that transmits through the block is offset in two directions relative to the beam (100) which enters the block. This is illustrated in FIG. 5a by the two beam offsets labeled OS1 and OS2, corresponding to offsets in the x-y plane and x-z plane, respectively. The magnitudes of OS1 and OS2 are dependent upon the respective rotation angles Δ1 and Δ2 of the rotating block (170). The rotating block (170) replaces the block (150) of the scatterometer configurations described previously in connection with FIGS. 3a, 3b, and 3c; otherwise these scatterometer configurations operate in essentially the same manner as previously described.

Figure 5B:
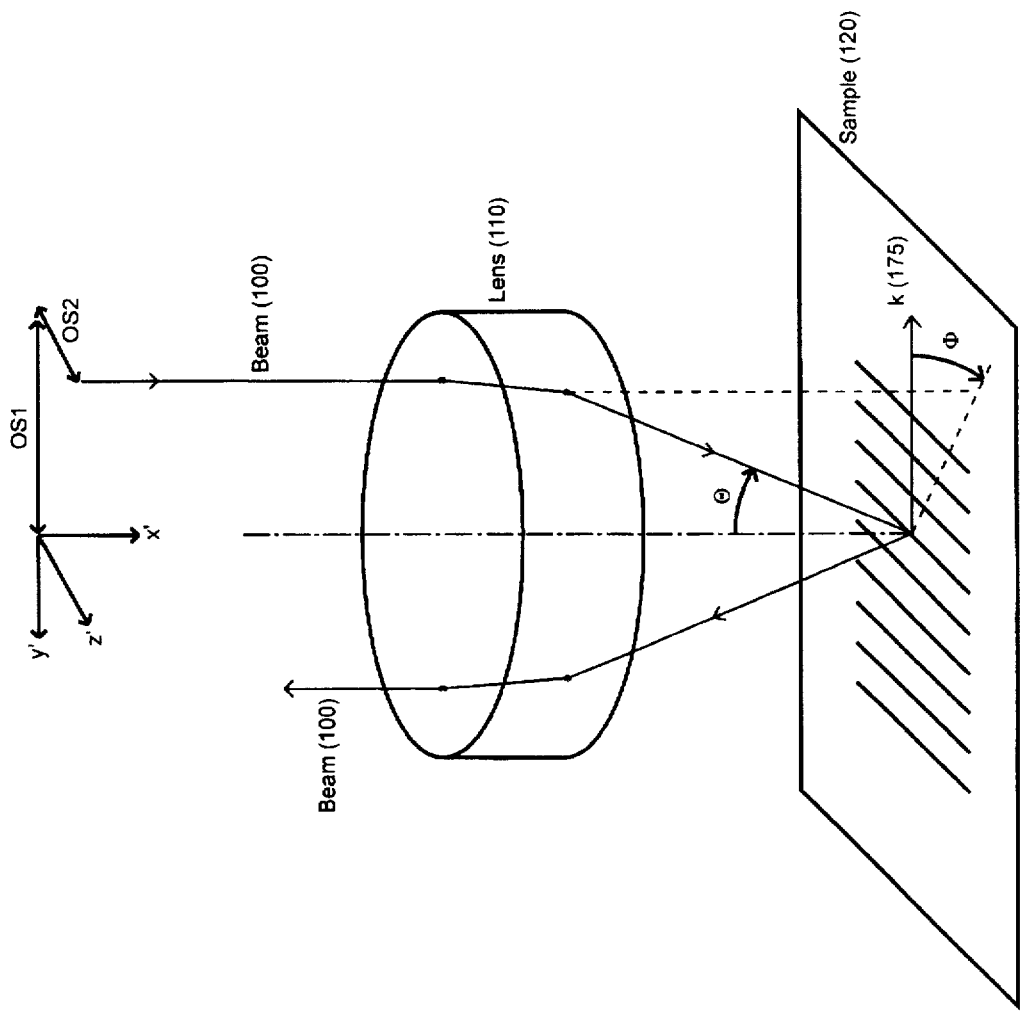
FIG. 5b is a pictorial diagram in accordance with the present invention, illustrating the geometry involved in illuminating the sample under separate control of the angle of incidence, $\Theta$, and $\Phi$, the angle between the grating vector and the incident beam.

FIG. 5b illustrates how the biaxial rotation of the block (170) causes the beam to be directed to different points in the plane of the entrance aperture of the lens (110). The plane of the entrance aperture of the lens (110) is parallel to the plane defined by the y'-z' axes, and the lens axis is in the x'-y' plane shown in FIG. 5b. In turn, the beam that illuminates the sample lies within a cone that is determined by the f/# of the lens (110). The incident beam makes an angle Θ with the normal to the sample and angle Φ with the grating vector, k (175), as illustrated in FIG. 5b. The grating vector, k (175), is in the plane of the sample (120) and in the direction normal to the lines of one of the sets of periodic structure comprising the sample (120). This is the two-dimensional extension of the one-dimensional illumination arrangements discussed in connection with FIGS. 3a, 3b, and 3c. More specifically, the nonzero value of Δ2 causes Φ to be nonzero. Diffraction in the general case of Φ being nonzero is called "conical diffraction". Measurements of the diffraction order intensities are made for one or more combinations of Δ1 and Δ2 to provide diffraction data over a range of values of Θ and Φ. Note that the x-y axes and the x'-y' axes lie in the same plane. The arrangements illustrated in FIGS. 5a and 5b thus provide a means to investigate the conical diffraction characteristics of a sample, with precise and independent control of Θ and Φ, that does not require moving the sample.

Figure 6A:
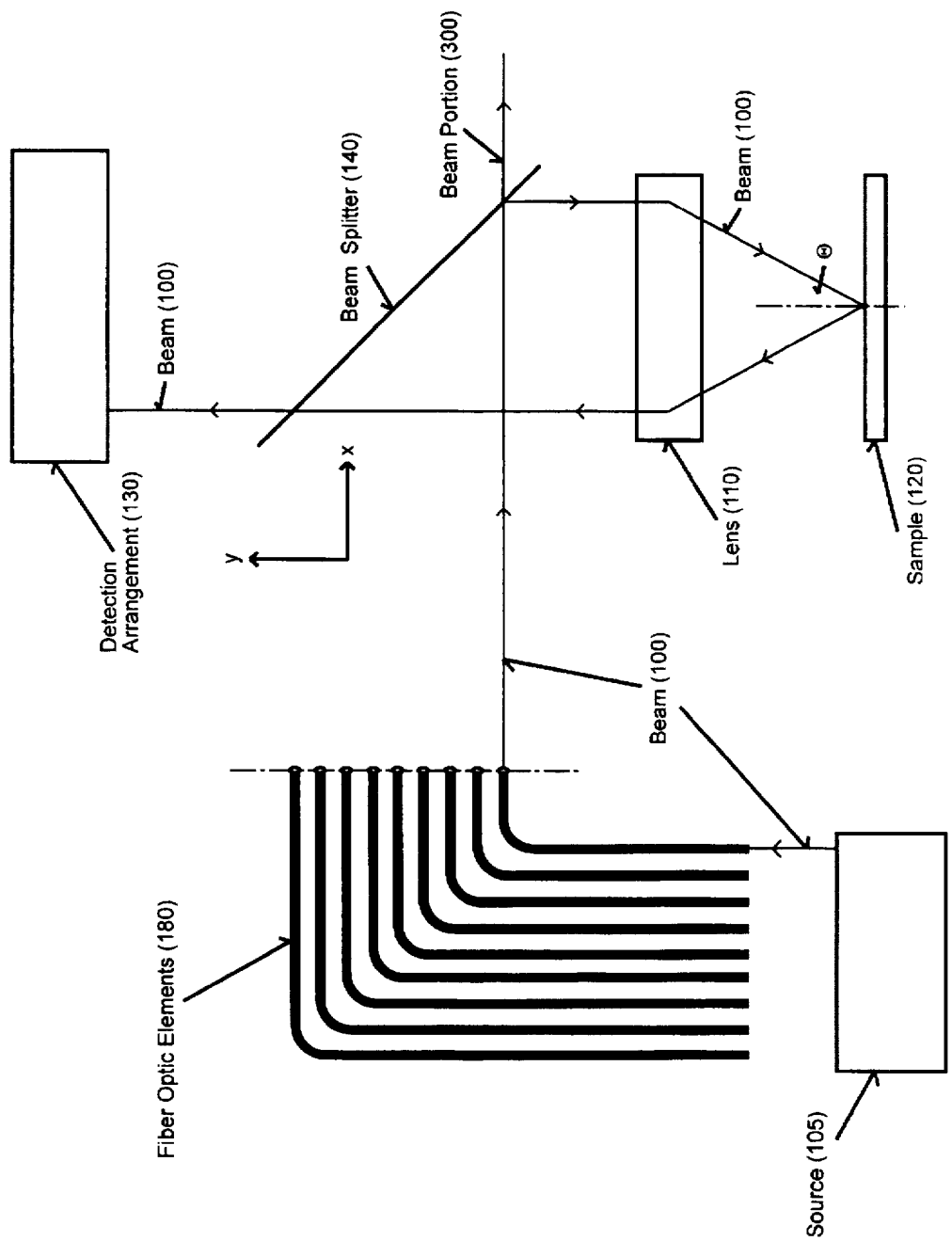
FIG. 6a is a pictorial diagram of a lens scatterometer system in accordance with the present invention, illustrating the use of a lens, beam splitter, fiber optic assembly, and light detection assembly for characterizing light that is diffracted from the sample.

FIG. 6a illustrates a lens scatterometer arrangement which utilizes one or more fiber optic elements (180) to comprise an array that provides beams of light. The array of fiber optic elements (180) is appropriately configured to provide beams (100) that are directed to different points of the entrance aperture of the lens (110), such that the sample (120) is illuminated at one or more desired angles of incidence, Θ. For example, the lens scatterometer arrangement of FIG. 6a is similar to that of FIG. 3a, except that nine fiber optic elements are arranged in a linear array situated along the y-axis in place of the block (150). This will in turn provide illumination of the sample (120) at nine different angles of incidence, Θ, and the beams which illuminate the sample (120) also lie in the x-y plane, consistent with the discussion related to the lens scatterometer arrangement of FIG. 3a. FIG. 6b illustrates how the fiber optic elements (180) can be arranged in a two-dimensional array that is utilized in the lens scatterometer arrangement; for convenience the other elements of the lens scatterometer arrangement are not included in this FIG. 6b. In the figure, the fiber optic elements (180) are arranged in two lines contained in the y-z plane, with an included angle of α. This arrangement provides beams in a two-dimensional array that are directed to the entrance aperture of the lens (110). This, in turn, produces illumination of the sample (120) with two sets of beams (100), with the angle Φ of one set of beams different from Φ of the other set of beams by the same angle α, thus providing a means of characterizing the conical diffraction of the sample (120). The operation of the scatterometer configurations illustrated in FIGS. 6a and 6b is otherwise essentially the same as those described in connection with FIGS. 3a, 3b, and 3c.

The linear arrangements of fiber optic elements (180) illustrated in FIGS. 6a and 6b were shown for illustration. Similarly, illustrating nine fiber optic elements (180) in each of the linear arrangements illustrated in FIGS. 6a and 6b was for purposes of illustration. Finally, showing the fiber optics elements (180) centered about the axis of the lens (110) was for purposes of illustration. The fiber optic elements (180) can be arranged an any desired manner, in curved or planar arrays that contain fewer or greater than nine fiber optic elements. Similarly, the arrays of fiber optic elements (180) are not required to be situated in the manner discussed previously, and they might be made to rotate or move laterally to provide for illumination at desired angles Θ and Φ. Because of their small size, many fiber optic elements can be arranged to provide high resolution of Θ and Φ.

Each fiber optic element is appropriately finished to provide a beam that is either collimated or focused a desired distance from the end of the element. This could consist of a simple lens attached to the output end of the fiber. A gradient index (grin) lens could also be utilized for this purpose. A lens array can be used for this purpose when a large number of fiber optics elements is utilized.

The fiber optic elements (180) can be illuminated, or activated, at their input ends in a number of manners. In one arrangement of the invention, each fiber optic element (180) is individually illuminated with the beam from the light source (105). In this arrangement, either the beam is scanned, or the fibers are moved to couple the beam into each fiber element (180). For this arrangement the diffraction order intensity measurements are performed in a sequential manner, as each fiber optic element is illuminated. An alternative arrangement involves illuminating the input ends of two or more fiber elements simultaneously. In this case, the diffraction order intensity measurements are performed simultaneously for those two or more fiber elements (180) that are illuminated. This is repeated, as necessary until all fiber elements (180) have been illuminated, and the corresponding diffraction order intensity measurements have been performed. The detector device necessarily provides the required spatial resolution in this situation. Still another arrangement of the invention involves use of individual light sources coupled to the input ends of each of the fiber optic elements (180). The most practical source for this application is a laser diode. Laser diodes are available commercially in arrays that can be utilized for this purpose. The light sources can be individually controlled to illuminate the fibers in the desired manner that is consistent with optimal diffraction order measurement; any combination of sequential/simultaneous illumination is possible. For the purpose of illustration, FIGS. 6a shows one fiber optic element being illuminated, and FIG. 6b shows two fiber optic elements being illuminated.

Figure 7A:
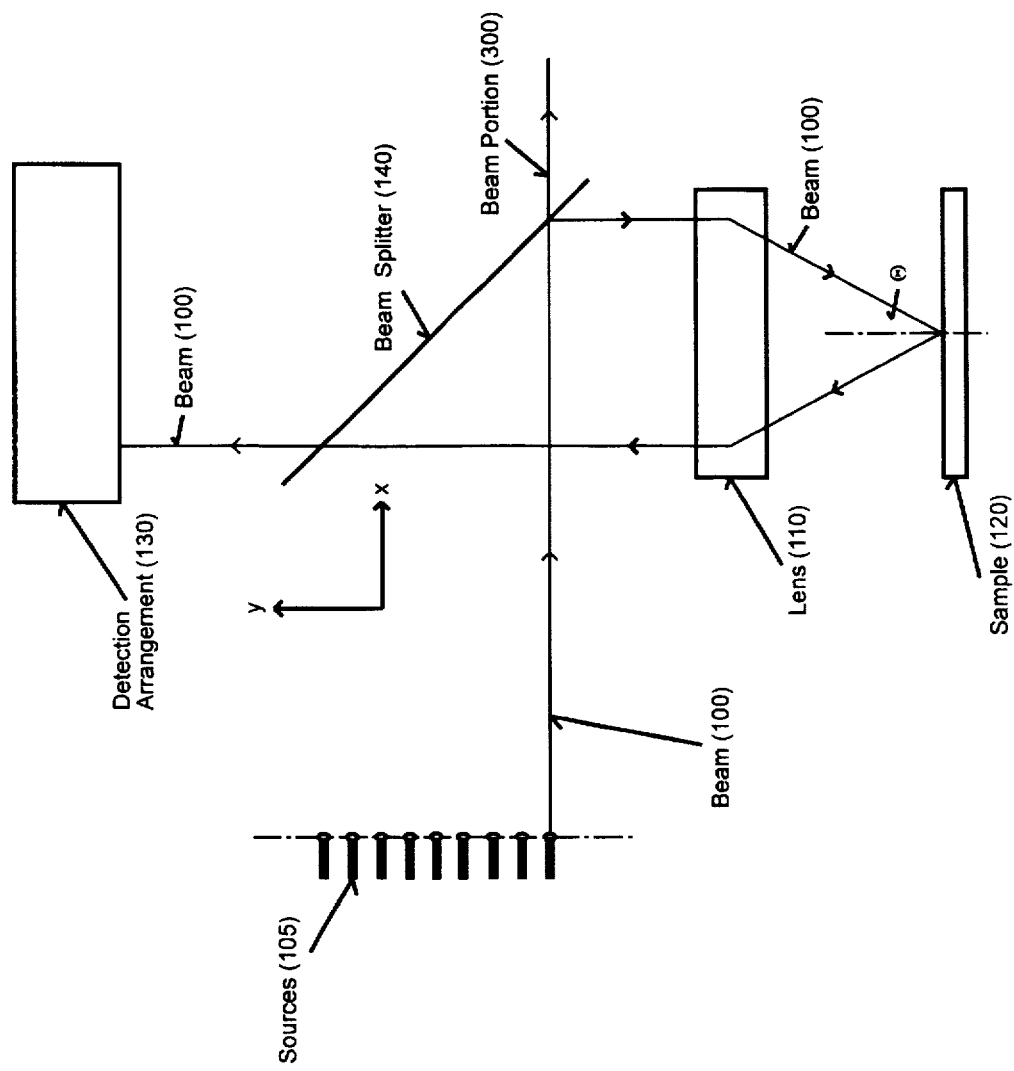
FIG. 7a is a pictorial diagram of a lens scatterometer system in accordance with the present invention, illustrating the use of a lens, beam splitter, laser array, and light detection assembly for characterizing light that is diffracted from the sample.
Figure 7B:
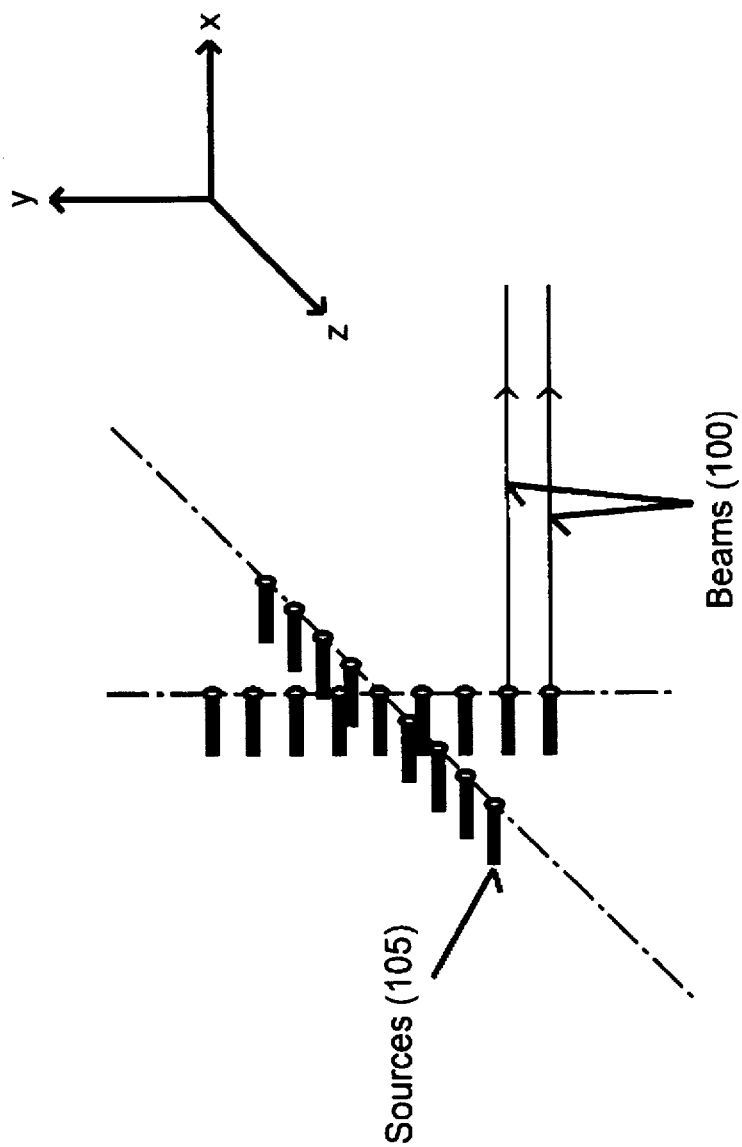
FIG. 7b is a pictorial diagram of a portion of a lens scatterometer system in accordance with the present invention, illustrating the use of a two dimensional source array for characterizing light that is conically diffracted from the sample.

FIG. 7a illustrates a lens scatterometer arrangement which utilizes more than one light source (105) to comprise an array that provides beams of light. The array of light sources (105) is appropriately configured to provide beams (100) that are directed to different points of the entrance aperture of the lens (110), such that the sample (120) is illuminated at more than one angle of incidence, Θ. Suitable light sources include diode lasers and light emitting diodes (LEDs). For example, the scatterometer arrangement of FIG. 7a is similar in operation to those illustrated in FIGS. 3a and 6a except that nine light sources are arranged in a linear array situated along the y-axis in place of the block (150). This will in turn provide illumination of the sample (120) at nine different angles of incidence, Θ. The beams which illuminate the sample (120) also lie in the x-y plane, consistent with the discussion related to the lens scatterometer arrangement of FIG. 3a. FIG. 7b illustrates how the light sources (105) can be arranged in a two-dimensional array that is utilized in the lens scatterometer arrangement; for convenience the other elements of the lens scatterometer arrangement are not included in this FIG. 7b. In the figure, the light sources (105) are arranged in two lines contained in the y-z plane, with an included angle of α. This arrangement provides beams in a two-dimensional array that are directed to the entrance aperture of the lens (110). This, in turn, produces illumination of the sample (120) with two sets of beams (100), with the angle Φ of one set of beams different from Φ of the other set of beams by the same angle α, thus providing a means of characterizing the conical diffraction of the sample (120). The operation of the scatterometer configurations illustrated in FIGS. 6a and 6b is otherwise essentially the same as those described in connection with FIGS. 3a, 3b, and 3c.

The linear arrangements of light sources (105) illustrated in FIGS. 7a and 7b were shown for illustration. Similarly, illustrating nine light sources (105) in each of the linear arrangements illustrated in FIGS. 7a and 7b was for purposes of illustration. Finally, showing the light sources (105) centered about the axis of the lens (110) was for purposes of illustration. The light sources (105) can be arranged an any desired manner, in curved or planar arrays that contain fewer or greater than nine light sources. Similarly, the arrays of light sources (105) are not required to be situated in the manner discussed previously, and they might be made to rotate or move laterally to provide for illumination at desired angles Θ and Φ. Because of their small size, many light sources can be arranged to provide high resolution of Θ and Φ. Each light source (105) is appropriately finished to provide a beam that is either collimated or focused a desired distance from the end of the element. This could consist of a lens attached to the output of the light source. A lens array can be used for this purpose when a large number of light sources is utilized. It is understood that other forms of a plurality of sources can be utilized within the bounds of this invention.

The light sources (105) of FIGS. 7a and 7b can be activated in a number of manners, similar to the invention of FIGS. 6a and 6b. In one arrangement of the invention, each light source (105) is individually activated to provide a beam, and the diffraction order intensity measurements are performed in a sequential manner. An alternative arrangement involves activating two or more light sources (105) simultaneously to provide two or more beams to illuminate the sample (120) simultaneously. In this case, the diffraction order intensity measurements are performed simultaneously for those two or more light sources that are activated. This is repeated, as necessary, until all light sources (105) have been activated, and the corresponding diffraction order intensity measurements have been performed. The detector device necessarily provides the required spatial resolution in this situation.

Figure 8A:
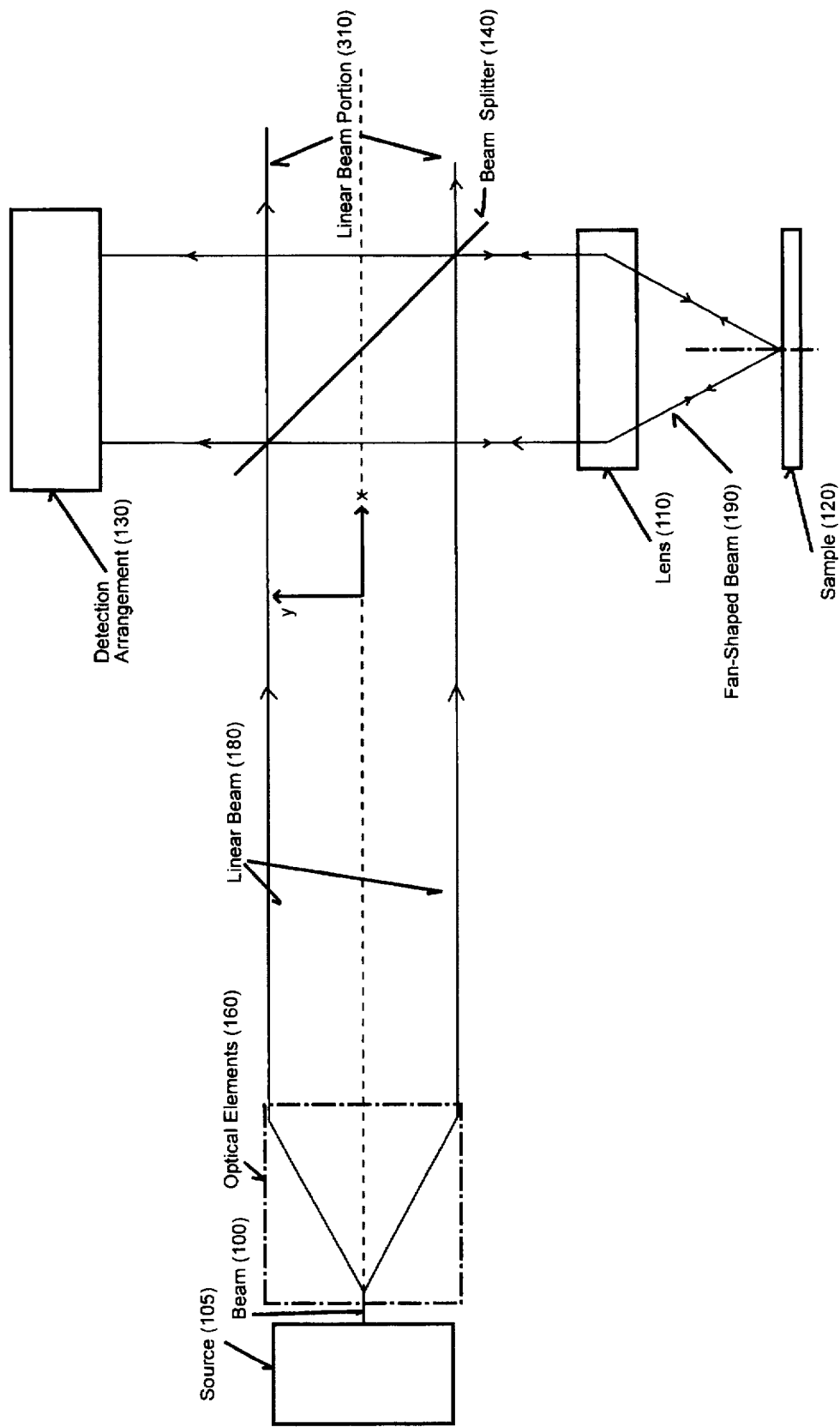
FIG. 8a is a pictorial diagram of a lens scatterometer system in accordance with the present invention, illustrating the use of a lens, beam splitter, linear beam, and light detection assembly for characterizing light that is diffracted from a sample.

FIG. 8a illustrates a lens scatterometer arrangement which utilizes one light source (105) in conjunction with optical elements (160) to provide a linear beam (180). The term "linear beam" in this invention is understood to refer to a collimated beam which-when viewed in cross-section (i.e. observing the beam intensity in a plane that is orthogonal to the direction of propagation) forms a line. The linear beam (180) is distinguished from the beam (100) mentioned previously in that the cross-section of the linear beam (180) is a line, whereas the cross-section of the beam (100) is typically a circle or nearly a circle. The linear beam (180) is directed to the beam splitter (140) which directs the beam to the entrance aperture of the lens (110), in a manner similar to that previously discussed in connection with the arrangement illustrated in FIG. 3a. The linear beam (180) passes through the lens (110), and it becomes a converging, fan-shaped beam (190) which is focused at the sample (120). This provides the equivalent of simultaneous illumination of the sample (120) with a large number of beams (100) at a large number of angles of incidence, Θ. The fan-shaped beam (190) lies in the x-y plane in FIG. 8a, consistent with the discussion related to the lens scatterometer arrangement of FIG. 3a. The detection system (130) necessarily provides the required spatial resolution in this situation, as previously discussed.

In the scatterometer implementation illustrated in FIG. 8a, the optical elements (160) are constructed to convert the circular or near-circular beam (100) from the source (105) into a linear beam (180). The width of the linear beam (180) is typically the same or nearly the same as the diameter of the beam (100), and the height of the linear beam (180) is much greater than its width. For example, the beam (100) from a He-Ne or similar laser is approximately circular and 1 mm in diameter. The optical elements (160) can be configured to convert this beam (100) into a linear beam (180) which in cross-section is a line of 1 mm by 50 mm. This might be accomplished, for example, by utilizing cylindrical lenses in a simple telescope configuration, including such designs as Keplerian, Galilean, astronomical, or others. Other configurations of optical elements (160) can be envisioned. For example, a portion of the optical elements (160) can be located adjacent to, or incorporated within the source (105), as is the case for a simple diode laser equipped with line generating optics. The output of such a configuration is a fan-shaped beam. Sometimes called diode laser line projectors, these devices are commonly available from a number of manufacturers, including Melles Griot of Irvine, Calif. and Edmund Scientific of Barrington, N.J. In this configuration the remainder of the optical elements (160) would be comprised of a lens and possibly additional elements to collimate, or nearly collimate the fan-shaped beam, thus forming a linear beam (180).

The linear beam (180) might also be utilized to examine the conical diffraction characteristics of the sample as previously discussed in connection with FIGS. 5a and 5b. To accomplish this without moving the sample (120), the linear beam is rotated about an axis that is parallel to, or coincident with its direction of propagation (the x-axis shown in FIG. 8a). This might be achieved, for example, by making the optical elements (160) capable of rotating the linear beam (180) about the x-axis and might be achieved by simply rotating the optical elements (160). In this configuration it may also be desirable to rotate the source (105) in order to maintain the desired polarization of the light field of the linear beam (180).

Figure 8B:
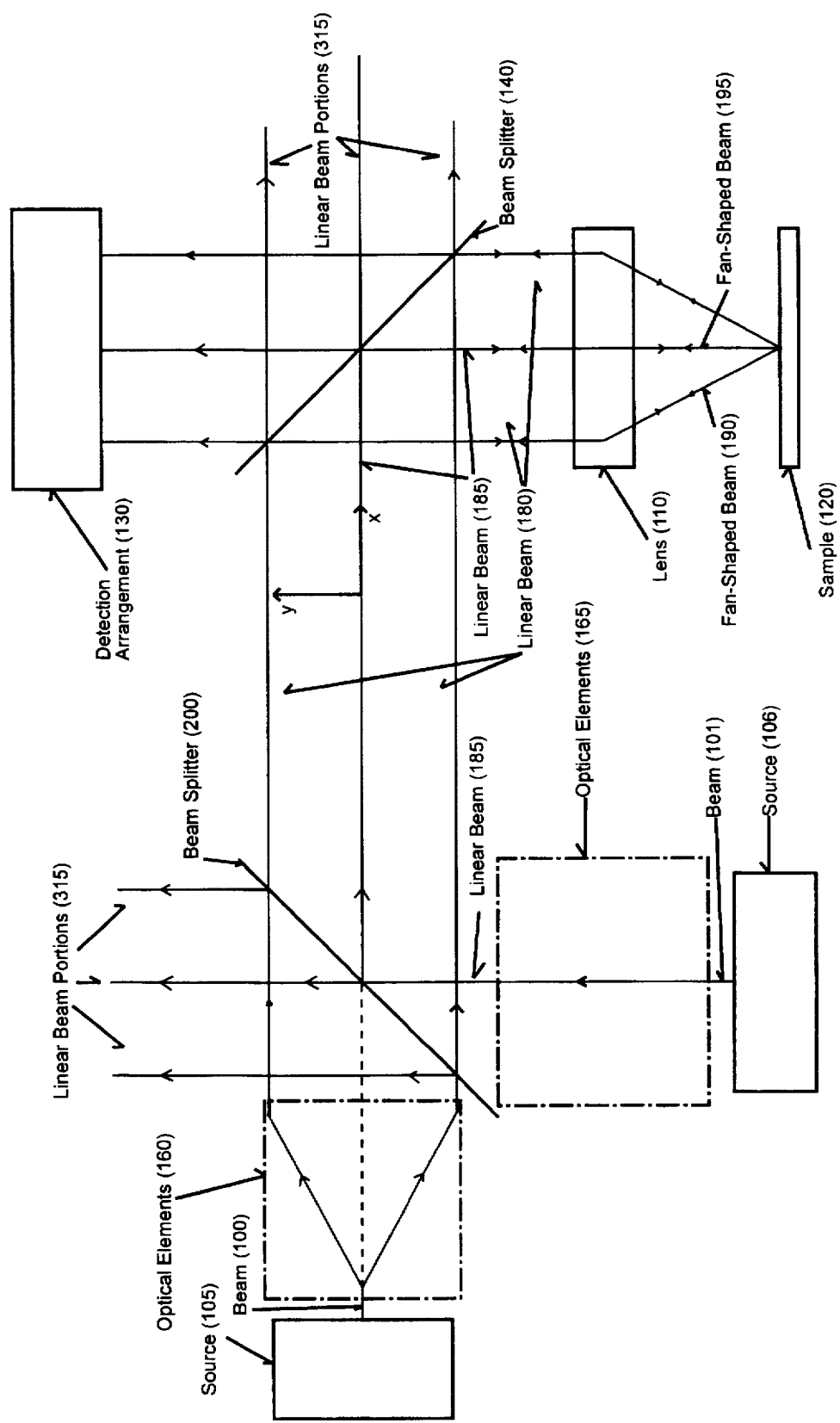
FIG. 8b is a pictorial diagram of a lens scatterometer system in accordance with the present invention, illustrating the use of a lens, two beam splitters, two linear beams, and light detection assembly for characterizing light that is conically diffracted from the sample.

FIG. 8b illustrates how two light sources (105) and (106), two sets of associated optical elements (160) and (165), and two linear beams (180) and (185) can be utilized in the lens scatterometer arrangement to examine the conical diffraction characteristics of the sample (120). The source (106) has the properties discussed previously in connection with the source (105). The sources (105) and (106) might be identical, or they might differ in some aspect such as emitting radiation at different wavelengths. The beam (101) has the properties described previously in connection with beam (100). The beams (100) and (101 ) might differ in some aspect, such as being comprised of radiation of different wavelengths. Similarly, the optical elements (165) have the same general properties as the optical elements (160), and the linear beam (185) has the same general properties as the linear beam (180). In FIG. 8b, the linear beam (180) from the source (105) is shown contained in the x-y plane as previously discussed. The linear beam (185) from the source (106) is shown perpendicular to the x-y plane and thus appears as a single line in FIG. 8b. Note that it is not a requirement that this linear beam be perpendicular to the x-y plane; the linear beam (185) can be arranged to make any angle with the x-y plane.

Referring to FIG. 8b, the beam splitter (200) directs portions of both linear beams (180) and (185) toward the beam splitter (140), and a portion of both linear beams (180) and (185) are reflected from the beam splitter (140) and directed to the entrance aperture of the lens (110). Two fan-shaped beams (190) and (195) are formed from the linear beams (180) and (185), respectively, and these fan-shaped beams (190) and (195) are focused on the sample. This provides the equivalent of illuminating the sample by two sets of beams, with each set illuminating the sample at many angles of incidence, Θ. The two sets of beams illuminate the sample at two different angles Φ. For the configuration illustrated in FIG. 8b, one value of Φ is 0°, and the other value of Φ is 90°. Note that in general that Φ can have values different from 0° and 90° by orienting the two linear beams (180) and (185) in a desired manner with respect to the x-y- plane. The operation of the scatterometer configurations illustrated in FIGS. 8a and 8b is otherwise essentially the same as those described in connection with FIGS. 3a, 3b, and 3c.

Figure 8C:
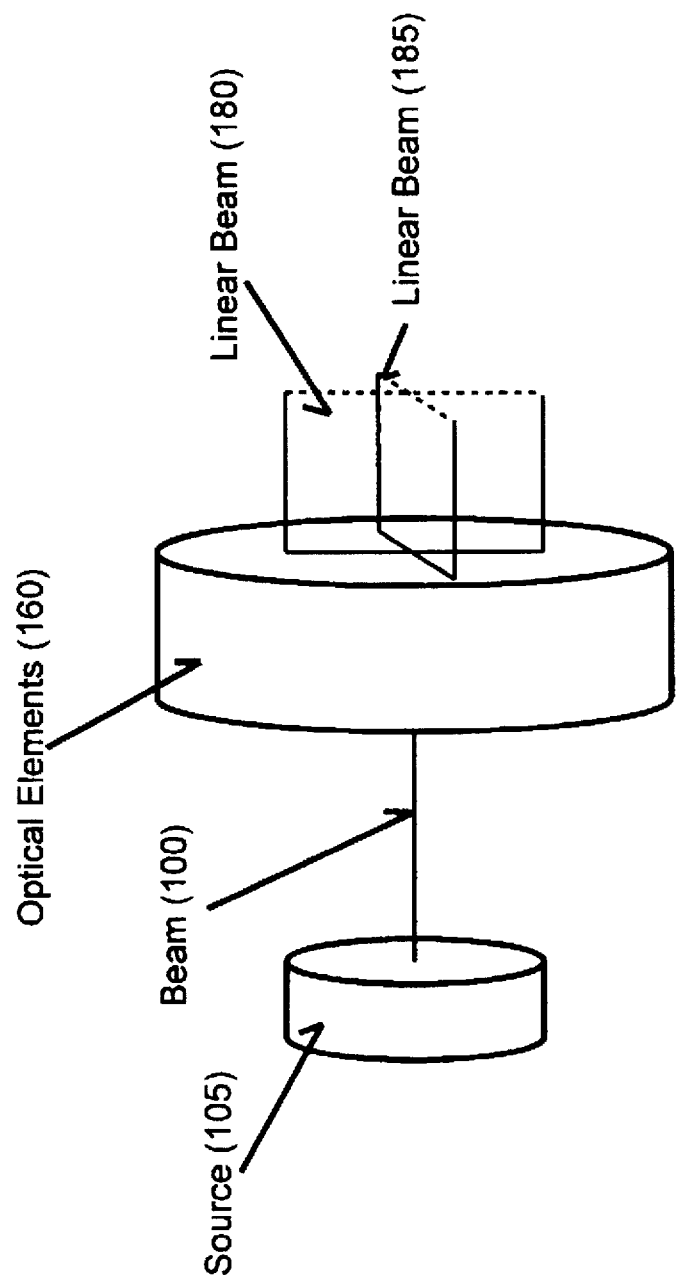
FIG. 8c is a pictorial diagram of a portion of a lens scatterometer system in accordance With the present invention, illustrating the use of a lens, beam splitter, two linear beams comprising a cross, and light detection assembly for characterizing light that is conically diffracted from the sample.

FIG. 8c illustrates the use of one light source (105) and optical elements (160) to provide two linear beams (180) and (185) for use in the lens scatterometer system. For convenience, only the source (105) and optical elements (160) are illustrated in FIG. 8c. The two linear beams (180) and (185) intersect and together comprise a beam which in cross-section forms a cross. This pattern is directed toward the beam splitter (140). A portion of the optical elements (160) can be located adjacent to, or incorporated within the source (105), as is the case for a simple diode laser equipped with cross-generating optics. Such a system is available commercially from Lasiris, Inc. of St. Laurent, Quebec, Canada. The source (105) and associated optical elements (160) illustrated in FIG. 8c are utilized in the scatterometer system shown in FIG. 8a to provide a measurement capability that is essentially the same as that of the scatterometer system illustrated in FIG. 8b. The conical diffraction properties of the sample (120) are characterized utilizing this apparatus without moving the sample.

Beams of other cross-section patterns are envisioned for use in the lens scatterometer system illustrated in FIG. 8a in essentially the same manner as the cross beam pattern described in connection with FIG. 8c. For example, the optical elements (160) can provide an array of beams that are directed toward beam splitter (140). Specifically, the cross-section pattern of the beam subsequent to exiting the optical elements (160) can be comprised of a one-dimensional or two-dimensional array of dots, a circle, an array of concentric circles, or some other desired pattern. Such patterns of light beams are possible by utilizing optical elements commercially from Lasiris, Inc. of St. Laurent, Quebec, Canada in conjunction with additional optical elements to comprise the optical elements (160).

Figure 9:
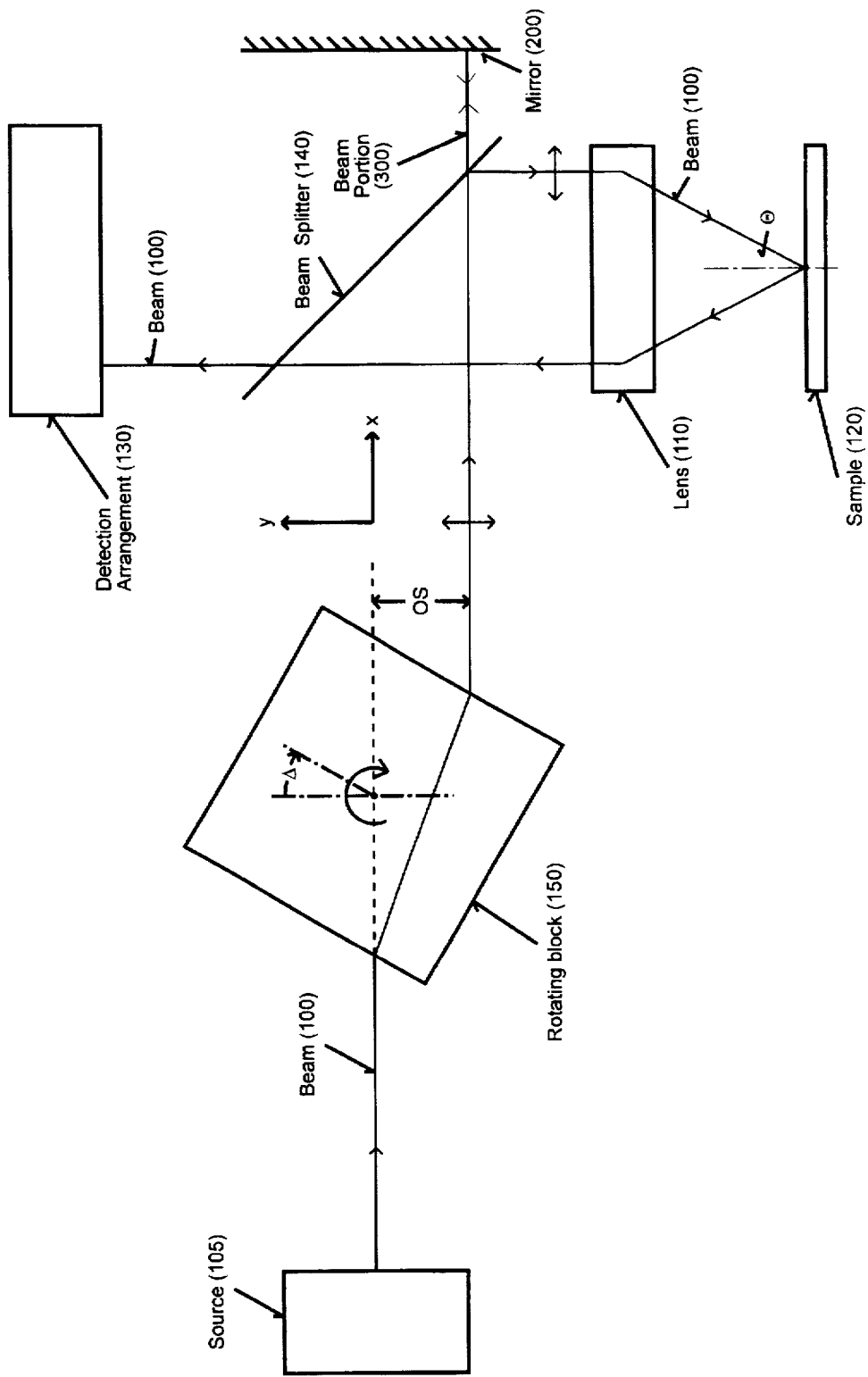
FIG. 9 is a pictorial diagram of a lens scatterometer system in accordance with the present invention, illustrating the use of a lens, beam splitter, rotating block, light detection system, and mirror for characterizing the intensity and phase of light that is diffracted from the sample.

FIG. 9 illustrates an additional mirror (200) that is added to the lens system scatterometer of FIG. 3a; the same modification can be made to the other systems discussed previously. The addition of the mirror (200) provides a significant increase in the information content of the measurements that are performed by providing a reference beam (210). The reference beam (210) allows the phase of the diffracted beams to be measured. The increased information that the arrangement of FIG. 9 provides is useful for determining additional properties of the diffracting sample (120).

In the arrangement of FIG. 9, the portion of the beam (100) from the source which illuminates the beam splitter but which is not directed to the lens (110) is allowed to illuminate the mirror (200) is termed the beam portion (300). For example, in FIG. 3a the beam from the rotating block that illuminates the beam splitter (140) and which is transmitted by said beam splitter (140) is the beam portion (300) which illuminates the mirror (200). Similarly, in the arrangement of FIG. 3b, the beam portion (300) that illuminates mirror (200) is that which comes from the rotating block and which is reflected by the beam splitter (140). The function of the mirror (200) is similar for the other scatterometer arrangements discussed previously. Continuing, the mirror (200) reflects this beam portion (300) back to the beam splitter (140). A portion thereof is reflected by the beam splitter (140) and becomes the so-called reference beam (210). It is a reference beam because its amplitude and phase does not depend upon, nor change with, the properties of the sample which is illuminated. The reference beam (210) propagates to the detection arrangement (130) where it is detected. As the angle of incidence of the scatterometer is changed, whether by the rotating the block (150), moving a mirror of the set of mirrors (160), or by other mechanisms, the mirror (200) operates in the manner just described to furnish a reference beam (210) to the detection arrangement (130) for all angles of incidence at which the sample (120) is illuminated.

The arrangement of FIG. 9 is similar to the well-known Twyman-Green and Michelson interferometer systems that are described in text books on optics. Teachings from these references can be utilized to understand the manner in which the reference beam (210) contributes additional information to the measurements performed in utilizing the lens system scatterometer. There are two significant differences between these interferometer systems and the lens scatterometer system of FIG. 9 in the manner that the reference beam is utilized. The interferometers utilize the reference beam only in conjunction with the 0-order diffracted (specularly reflected) beam from the sample (120), while the lens scatterometer system illustrated in FIG. 9 utilizes the reference beam (210) for all diffraction orders (0-order, ±1-orders, etc.) which are detected. Second, interferometers do not involve changing the angle of incidence of the beam that illuminates the sample, whereas a primary function of the lens scatterometer is to vary the angle of incidence. As a result, interferometers utilize the reference beam for only one angle of incidence, typically 0 degrees, whereas the lens scatterometer utilizes the reference beam over a range of incidence angles.

Note that the mirror (200) can be constructed to contain a phase-shifting element that shifts the phase of the reference beam (210). The phase can be changed a desired amount with the application of an appropriate signal to the phase-shifting element. This phase-shifting of the reference beam (210) can be utilized during a measurement performed using the lens system scatterometer to contribute additional information concerning the sample (120) under investigation. The teachings from well-known books on optics can be utilized for understanding the way in which the phase-shifting technique can increase the information obtained in performing measurements of light diffracted from the sample (120). The phase-shifting element can, for example, be comprised of a piezo-electric crystal that is attached to the back surface of the mirror (200). An appropriate voltage applied to the piezo-electric crystal will cause the mirror (210) to be displaced toward the beam splitter (140), thus changing the phase of the reference beam (210).

Note that the lens scatterometer arrangements discussed above can be used to characterize samples which are unpatterned. In this situation in which the sample has no periodic structure, only the 0-order diffracted beams are diffracted, with one reflected from the sample and one transmitted into the sample. The intensities of one or both of these beams is measured. This amounts to characterizing the reflectance and transmittance of the sample as a function of angle of the incident beam. Analysis of this information yields information concerning the optical properties of the sample, such as the thickness and refractive index of thin films which might be part of the sample.

The elements of the lens scatterometer system are typically controlled by a simple computer, such as a so-called PC or workstation. This control includes rotation of the block (150) or block (170), or motion of the mirror of the mirror set (160), as well as sample positioning, beam source activation, collection of data from the detector arrangement, and overall system coordination. In addition, the computer can perform analysis of the data that is collected.

We claim:

1. An optical scatterometer system for characterizing the diffraction properties of a sample material by varying the angle of incidence of a light beam from a source without moving the sample material, the optical scatterometer comprising:

light source means for transmitting one or more source light beams;

a beam splitter positioned to direct the one or more source light beams diffracted by the sample material;

a lens positioned such that the sample material is located in a back focal plane of the lens, the lens being further positioned to receive the one or more source light beams directed by the beam splitter, to transmit the one or more source light beams to illuminate the sample material, to receive the one or more light beams diffracted by the sample material, and to transmit the one or more light beams diffracted by the sample material to the beam splitter;

one or more detection systems positioned to receive and characterize the one or more light beams diffracted by the sample material; and beam direction means positioned between the light source means and the beam splitter for scanning the one or more source light beams along a line in an entrance aperture of the lens to thereby direct the one or more source light beams transmitted by the light source means to selected different points along said line in the entrance aperture of the lens.

2. An optical scatterometer system as in claim 1 wherein the beam direction means comprises a rotatable block transparent at the wavelength of the source light beam.

3. An optical scatterometer system as in claim 2 wherein the rotatable block is arranged for rotation about one axis.

4. An optical scatterometer system as in claim 2 wherein the rotatable block is arranged for rotation about two axes to enable characterization of conical diffraction characteristics of the sample material.

5. An optical scatterometer system as in claim 1 wherein the beam direction means comprises a set of mirrors.

6. An optical scatterometer system as in claim 5 wherein one or more mirrors of the set of mirrors are movable in a predetermined manner.

7. An optical scatterometer system as in claim 1 wherein the beam direction means comprises an array of fiber optic elements.

8. An optical scatterometer system as in claim 7 wherein the array of fiber optic elements comprises a one-dimensional array.

9. An optical scatterometer system as in claim 7 wherein the array of fiber optic elements comprises a two-dimensional array.

10. An optical scatterometer system as in claim 1 wherein each of the one or more detection systems includes a single detection element for providing an integrated characterization of the one or more light beams diffracted by the sample material.

11. An optical scatterometer system as in claim 1 wherein each of the one or more detection systems includes an array of detection elements for providing one-dimensional characterization of the one or more light beams diffracted by the sample material.

12. An optical scatterometer system as in claim 11 wherein the array of detection elements comprises a CCD array.

13. An optical scatterometer system as in claim 1 wherein the array of detection elements comprises a photodiode array.

14. An optical scatterometer system as in claim 1 wherein the array of detection elements comprises a camera.

15. An optical scatterometer system as in claim 1 wherein each of the one or more detection systems includes an array of detection elements for providing two-dimensional characterization of the one or more light beams diffracted by the sample material.

16. An optical scatterometer system as in claim 1 wherein the one or more detection systems comprises a videcon.

17. An optical scatterometer system as in claim 1 wherein the one or more detection systems comprises a nuvicon.

18. An optical scatterometer system as in claim 15 wherein the array of detection elements comprises a CCD array.

19. An optical scatterometer system as in claim 15 wherein the array of detection elements comprises a photodiode array.

20. An optical scatterometer system as in claim 15 wherein the array of detection elements comprises a camera.

21. An optical scatterometer system as in claim 1, further comprising a mirror for providing a reference light beam to in turn provide additional information regarding the sample material.

22. An optical scatterometer system for characterizing the diffraction properties of a sample material by varying the angle of incidence of a light beam from a source without moving the sample material, the optical scatterometer comprising:

light source means for transmitting a source light beam having a desired cross-sectional pattern;

a beam splitter positioned to direct the source light beam toward the sample material and to direct one or more light beams diffracted by the sample material;

a lens positioned such that the sample material is located in a back focal plane of the lens, the lens being further positioned to receive the source light beam directed by the beam splitter such that the source light beam simultaneously illuminates all points in said pattern in an entrance aperture of the lens and such that a maximum linear dimension of the illuminated pattern comprises a substantial portion of a diameter of said entrance aperture, to transmit the source light beam to illuminate the sample material, to receive the one or more light beams diffracted by the sample material, and to transmit the one or more light beams diffracted by the sample material.

23. An optical scatterometer system as in claim 22 wherein the light source means is operative for transmitting a light beam of linear cross-section.

24. An optical scatterometer system as in claim 22 wherein the light source means is operative for transmitting two light beams of linear cross-section for enabling characterization of conical diffraction characteristics of the sample material.

25. An optical scatterometer system as in claim 24 wherein the light source means comprises at least one light source operative for transmitting two intersecting source light beams that are each of linear cross-section.

26. An optical scatterometer system as in claim 24 wherein the light source means comprises at least one light source operative for transmitting an array of source light beams.

27. An optical scatterometer system as in claim 22, further comprising a mirror for providing a reference light beam to in turn provide additional information regarding the sample material.

28. An optical scatteromter system for characterizing the diffraction properties of a sample material by varying the angle of incidence of a light beam from a source without moving the sample material, the optical scatterometer comprising:

light source means for transmitting a plurality of source light beams;

a beam splitter positioned to direct the plurality of source light beams toward the sample material and to direct one or more light beams diffracted by the sample material;

a lens positioned such that the sample material is located in a back focal plane of the lens, the lens being further positioned to receive the plurality of source light beams directed by the beam splitter, to transmit the plurality of source light beams to illuminate the sample material, to receive the one or more light beams diffracted by the sample material, and to transmit the one or more light beams diffracted by the sample material to the beam splitter; and one or more detection systems positioned to receive and characterize the one or more light beams diffracted by the sample material;

said light source means being operative for directing the plurality of source light beams to selected different points of an entrance aperture of the lens to thereby illuminate the sample material at multiple angles of incidence.

29. An optical scatterometer system as in claim 28 wherein the light source means comprises a one-dimensional array of light sources.

30. An optical scatterometer system as in claim 28 wherein the light source means comprises a two-dimensional array of light sources.

* * * * *